(12) United States Patent
Lee et al.

(10) Patent No.: US 7,803,353 B2
(45) Date of Patent: Sep. 28, 2010

(54) ORAL CARE COMPOSITIONS HAVING IMPROVED CONSUMER AESTHETICS AND TASTE

(75) Inventors: Kuo-Chung Mark Lee, Mason, OH (US); James Carl Grimm, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/714,445

(22) Filed: Mar. 6, 2007

(65) Prior Publication Data

US 2007/0231278 A1    Oct. 4, 2007

Related U.S. Application Data

(60) Provisional application No. 60/786,942, filed on Mar. 29, 2006.

(51) Int. Cl.
*A61K 8/22* (2006.01)
*A61K 8/24* (2006.01)
*A61K 8/34* (2006.01)

(52) U.S. Cl. .............................. 424/49; 424/52; 424/53
(58) Field of Classification Search .............. 424/49–58
See application file for complete search history.

(56) References Cited

U.S. PATENT DOCUMENTS

| | | | |
|---|---|---|---|
| 4,157,384 A | 6/1979 | Watson et al. | |
| 4,431,631 A | 2/1984 | Clipper et al. | |
| 4,537,778 A | 8/1985 | Clipper et al. | |
| 4,684,517 A | 8/1987 | Clipper et al. | |
| 4,696,757 A | 9/1987 | Blank et al. | |
| 4,788,052 A | 11/1988 | Ng et al. | |
| 4,839,152 A | 6/1989 | Vella et al. | |
| 4,839,157 A | 6/1989 | Ng et al. | |
| 4,849,213 A | 7/1989 | Schaeffer | |
| 4,895,721 A | 1/1990 | Drucker | |
| 5,009,893 A | 4/1991 | Cherukuri et al. | |
| 5,059,417 A | 10/1991 | Williams et al. | |
| 5,085,853 A | 2/1992 | Williams et al. | |
| 5,104,644 A | 4/1992 | Douglas | |
| 5,174,990 A | 12/1992 | Douglas | |
| 5,186,926 A | 2/1993 | Williams et al. | |
| 5,310,546 A | 5/1994 | Douglas | |
| 5,348,750 A | 9/1994 | Greenberg | |
| 5,372,824 A | 12/1994 | Record et al. | |
| 5,451,346 A * | 9/1995 | Amou et al. | 252/186.23 |
| 5,451,404 A | 9/1995 | Furman | |
| 5,663,460 A | 9/1997 | Yamamoto et al. | |
| 5,695,746 A | 12/1997 | Garlick et al. | |
| 5,698,181 A | 12/1997 | Luo | |
| 5,725,865 A | 3/1998 | Mane et al. | |
| 5,811,080 A | 9/1998 | Burgess et al. | |
| 5,820,854 A * | 10/1998 | Glandorf | 424/52 |
| 5,843,466 A | 12/1998 | Mane et al. | |
| 6,042,812 A * | 3/2000 | Sanker et al. | 424/49 |
| 6,348,187 B1 | 2/2002 | Pan et al. | |
| 6,391,886 B1 | 5/2002 | Lee | |
| 6,627,233 B1 | 9/2003 | Wolf et al. | |
| 6,897,195 B2 | 5/2005 | Su et al. | |
| 6,916,463 B2 | 7/2005 | Lee et al. | |
| 2006/0013837 A1* | 1/2006 | Haines | 424/401 |

* cited by examiner

*Primary Examiner*—Frederick Krass
*Assistant Examiner*—Walter E Webb
(74) *Attorney, Agent, or Firm*—Emelyn L. Hiland

(57) ABSTRACT

The present invention relates to peroxide containing oral care compositions containing a flavor system that effectively masks the undesirable taste and sensations due to peroxide. The flavor system comprises menthol, at least one other secondary coolant and selected flavor chemicals that together provide a stable flavor profile and a high impact refreshing taste and sensation. The secondary coolant is selected from carboxamides, ketals, diols, menthyl esters and mixtures thereof.

9 Claims, No Drawings

ORAL CARE COMPOSITIONS HAVING IMPROVED CONSUMER AESTHETICS AND TASTE

CROSS REFERENCE TO RELATED APPLICATION

This application claims the benefit of U.S. Provisional Application No. 60/786,942, filed Mar. 29, 2006.

TECHNICAL FIELD

The present invention relates to oral care compositions containing a flavor system that effectively masks the undesirable taste and sensations due to certain ingredients. In particular, the ingredient with undesirable aesthetics is peroxide, which is included in dentifrice and mouthrinse compositions for its whitening and antimicrobial benefits. The taste and mouthfeel of oral care products are particularly important for consumer acceptability and compliance since use of these products necessarily involve fairly long residence time in the mouth for efficacy.

BACKGROUND OF THE INVENTION

Oral care products such as dentifrice and mouthrinse are routinely used by consumers as part of their oral care hygiene regimens. It is well known that oral care products can provide both therapeutic and cosmetic hygiene benefits to consumers. Therapeutic benefits include caries prevention which is typically delivered through the use of various fluoride salts; gingivitis prevention by the use of an antimicrobial agent such as triclosan, stannous fluoride, or essential oils; or hypersensitivity control through the use of ingredients such as strontium chloride or potassium nitrate. Cosmetic benefits provided by oral care products include the control of plaque and calculus formation, removal and prevention of tooth stain, tooth whitening, breath freshening, and overall improvements in mouth feel impression which can be broadly characterized as mouth feel aesthetics. Calculus and plaque along with behavioral and environmental factors lead to formation of dental stains, significantly affecting the aesthetic appearance of teeth. Behavioral and environmental factors that contribute to teeth staining propensity include regular use of coffee, tea, cola or tobacco products, and also the use of certain oral products containing ingredients that promote staining, such as cationic antimicrobials and metal salts.

Thus daily oral care at home requires products with multiple ingredients working by different mechanisms to provide the complete range of therapeutic and aesthetic benefits, including anticaries, antimicrobial, antigingivitis, antiplaque and anticalculus as well as antiodor, mouth refreshment, stain removal, stain control and tooth whitening. In order for oral care products for daily use such as dentifrice and rinses to provide complete oral care it is necessary to combine actives and additives, many of which have the disadvantage of causing negative aesthetics during use, in particular unpleasant taste and sensations and stain promotion. The unpleasant taste and mouth sensations have been described as having one or more of bitter, metallic, astringent, salty, numbing, stinging, burning, prickling, and evens irritating aspects. Typical ingredients for oral care use that are associated with these aesthetic negatives include antimicrobial agents such as cetyl pyridinium chloride, chlorhexidine, stannous and zinc salts; tooth bleaching agents such as peroxides; antitartar agents such as pyrophosphate, tripolyphosphate and hexametaphosphate; and excipients such as baking soda and surfactants. To mitigate the aesthetic negatives from these ingredients, oral care products are typically formulated with flavoring agents and sweeteners to taste as good as possible and be consumer acceptable.

Although there have been many advances in oral care product formulations in recent years, there is still a need for improved products, particularly peroxide containing products with improved aesthetics and taste. Flavoring peroxide containing products' presents significant challenges for the formulator because the unpleasant taste and sensations derived from peroxide are difficult to mask and because many traditional flavor components are not sufficiently stable in the presence of peroxide. The present invention provides an improved flavor system comprising selected traditional flavor components combined with a mixture of menthol with at least one other coolant. The improved flavor system effectively masks the unpleasant taste and sensations derived from peroxide and provide a refreshing taste and sensation preferred by consumers.

SUMMARY OF THE INVENTION

The present invention is directed to oral care compositions comprising
(a) a, peroxide source,
(b) a flavor composition comprising menthol, a secondary coolant and one or a mixture of selected flavor components that maintain a stable profile in the presence of peroxide, and
(c) an orally-acceptable carrier comprising excipients and diluents, which are capable of being commingled with the peroxide without substantially interacting with the peroxide in a manner which would substantially reduce the stability of the composition. The compositions have a stable, well-rounded flavor profile and are pleasant tasting and refreshing, thereby encouraging user compliance and frequent use.

These and other features, aspects, and advantages of the present invention will become evident to those skilled in the art from the detailed description which follows.

DETAILED DESCRIPTION OF THE INVENTION

While the specification concludes with claims particularly pointing out and distinctly claiming the invention, it is believed that the present invention will be better understood from the following description.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

Herein, "comprising" means that other steps and other components which do not affect the end result can be added. This term encompasses the terms "consisting of" and "consisting essentially of."

As used herein, the word "include," and its variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, denture product, mouthspray, lozenge, chewable tablet or chewing gum. The oral care composition may also be incorporated onto strips or films for direct application or attachment to oral surfaces.

The term "dentifrice", as used herein, means paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally acceptable carrier or excipients" includes materials safe and effective materials and conventional additives used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavor system, sweetening agents, xylitol, coloring agents, and mixtures thereof.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed.

Herein, the terms "tartar" and "calculus" are used interchangeably and refer to mineralized dental plaque biofilms.

The essential and optional components of the present compositions are described in the following paragraphs.

Peroxide Source

The present compositions contain a peroxide source as a first essential ingredient for its many benefits to the oral, cavity. It has long been recognized that hydrogen peroxide and other peroxygen-containing agents are effective in curative and/or prophylactic treatments with respect to caries, dental plaque, gingivitis, periodontitis, mouth odor, tooth stains, recurrent aphthous ulcers, denture irritations, orthodontic appliance lesions, postextraction and postperiodontal surgery, traumatic oral lesions and mucosal infections, herpetic stomatitis and the like. Peroxide-containing agents in the oral cavity exert a chemomechanical action generating thousands of tiny oxygen bubbles produced by interaction with tissue and salivary enzymes. The swishing action of a mouthrinse enhances this inherent chemomechanical action. Such action has been recommended for delivery of other agents into infected gingival crevices. Peroxide mouthrinses prevent colonization and multiplication of anaerobic bacteria known to be associated with periodontal disease. However, compositions containing hydrogen peroxide or other peroxide releasing compounds generally provide disagreeable taste and mouth sensations. These sensations have been described as stinging, prickling and irritating, similar to that experienced when the tongue comes into contact with sharp flavors or highly carbonated liquids such as club soda. In addition peroxides interact with other common excipients therein and tend to be unstable in storage, continuously losing the capacity to release active or nascent oxygen over relatively short periods of time, and tend to diminish or destroy the desired function of such excipients. Among such excipients are flavors, sensory materials and coloring agents added to enhance the acceptability of the oral care product to those in need of an oral peroxidizing or bleaching treatment.

Peroxide sources include peroxide compounds, perborates, percarbonates, peroxyacids, persulfates, and combinations thereof. Suitable peroxide compounds include hydrogen peroxide, urea peroxide, calcium peroxide, sodium peroxide, zinc peroxide and mixtures thereof. A preferred percarbonate is sodium percarbonate. Preferred persulfates are oxones. Preferred peroxide sources for use in dentifrice formulations include calcium peroxide and urea peroxide. Hydrogen peroxide and urea peroxide are preferred for use in mouthrinse formulations. The following amounts represent the amount of peroxide raw material, although the peroxide source may contain ingredients other than the peroxide raw material. The present composition may contain from about 0.01% to about 30%, preferably from about 0.1% to about 10%, and more preferably from about 0.5% to about 5% of a peroxide source, by weight of the composition.

Flavor System

A flavor system that effectively masks the unpleasant taste and sensations due to the peroxide component is the second essential component of the composition. Pleasant tasting compositions improve user compliance to prescribed or recommended use of peroxide containing products. The present flavor system comprises menthol as a first coolant in combination with at least one secondary cooling agent along with selected traditional flavor components that have been found to be relatively stable in the presence of peroxide. By "stable" herein is meant that the flavor character or profile does not significantly change or is consistent during the life of the product. Thus, the flavor components may undergo some degradation during the life of the product; however this does not result in a significant change in the flavor character or profile or its acceptability. The combination of the selected flavoring agents with the coolants provides a high-impact refreshing sensation with a well-rounded flavor profile that effectively masks the unpleasant peroxide taste and sensations.

The oral care composition will comprise from about 0.04% to 1.5% total coolants (menthol+secondary coolant) with at least about 0.015% menthol by weight. Typically, the level of menthol in the final composition ranges from about 0.015% to about 1.0% and the level of secondary coolant(s) ranges from about 0.01% to about 0.5%. Preferably, the level of total coolants ranges from about 0.03% to about 0.6%.

Suitable secondary cooling agents or coolants to be used with menthol include a wide variety of materials such as carboxamides, ketals, diols, menthyl esters and mixtures thereof. Examples of secondary coolants in the present compositions are the paramenthan carboxamide agents such as N-ethyl-p-menthan-3-carboxamide, known commercially as "WS-3", N,2,3-trimethyl-2-isopropylbutanamide, known as, "WS-23", and others in the series such as WS-5, WS-11, WS-14 and WS-30. Additional suitable coolants include 3-1-menthoxypropane-1,2-diol known as TK-10 manufactured by Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Manè. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Traditional flavor components that have been found to be relatively stable in the presence of peroxide include methyl salicylate, ethyl salicylate, methyl cinnamate, ethyl cinnamate, butyl cinnamate, ethyl butyrate, ethyl acetate, methyl anthranilate, iso-amyl acetate, iso-armyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, alpha-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone and mixtures thereof. Generally suitable flavoring agents are those containing structural features and functional groups that are less prone to oxidation by peroxide. These include derivatives of flavor chemicals that are saturated or contain stable aromatic rings or ester groups. Also suitable are flavor chemicals that may undergo some oxidation or degradation without resulting in a significant change in the flavor character or profile. It is preferred that the flavor chemicals including menthol are provided as single or purified chemicals rather than supplied in the composition by addition of natural oils or extracts such as peppermint, spearmint or wintergreen oils as these sources may contain other components that are relatively unstable and may degrade in the presence of peroxide. Such degradation may significantly alter the desired flavor profile and result in a less acceptable product from an organoleptic standpoint. In a blind use test, consumers preferred a peroxide rinse (Example IC below) flavored with an artificial mint containing only purified chemicals than the same formula flavored with a similar mint flavor containing some natural oils, although both flavors were acceptable. Thus even if flavor chemicals undergo degradation and produce off-notes, the present coolant combination appears to effectively mask such off-notes. Flavoring agents are generally used in the compositions at levels of from about 0.001% to about 5%, by weight of the composition.

The flavor system will typically include a sweetening agent. Suitable sweeteners include those well known in the art, including both natural and artificial sweeteners. Some suitable water-soluble sweeteners include monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include Dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2, 2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) can be used. A composition preferably contains from about 0.1% to about 10% of sweetener, preferably from about 0.1% to about 1%, by weight of the composition.

In addition the flavor system may include salivating agents, warming agents, and numbing agents. These agents are present in the compositions at a level of from about 0.001% to about 10%, preferably from about 0.1% to about 1%, by weight of the composition. Suitable salivating agents include Jambus manufactured by Takasago. Examples of warming agents are capsicum and nicotinate esters, such as benzyl nicotinate. Suitable numbing agents include benzocaine, lidocaine, clove bud oil, and ethanol.

In addition to the components described above, the present compositions may comprise additional optional components collectively referred to as orally acceptable carrier materials, which are described in the following paragraphs:

Orally Acceptable Carrier Materials

The orally acceptable carrier comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy.

The carriers or excipients of the present invention can include the usual and conventional components of dentifrices, non-abrasive gels, subgingival gels, mouthwashes or rinses, mouth sprays, chewing gums, lozenges and breath mints as more fully described hereinafter.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, etc. as disclosed in e.g., U.S. Pat. No. 3,988,433, to Benedict. Carrier materials for biphasic dentifrice formulations are disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U.S. Pat. Nos. 4,849, 213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955, to Grabenstetter et al. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910, issued, Mar. 30, 1993 and Sep. 7, 1993, respectively both to Damani. Carriers suitable for the preparation of compositions of the present invention are well known in the art. Their selection will depend on secondary considerations like taste, cost, and shelf stability, etc.

The compositions of the present invention may also be in the form of non-abrasive gels and subgingival gels, which may be aqueous or non-aqueous. In still another aspect, the invention provides a dental implement impregnated with the present composition. The dental implement comprises an implement for contact with teeth and other tissues in the oral cavity, said implement being impregnated with the present composition. The dental implement can be impregnated fibers-including dental floss or tape, chips, strips, films and polymer fibers.

In one embodiment, the compositions of the subject invention are in the form of dentifrices, such as toothpastes; tooth gels and tooth powders. Components of such toothpaste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion) and an anticalculus agent (from about 0.1% to about 13%). Tooth powders, of course, contain substantially all non-liquid components.

Other embodiments of the subject invention are liquid products, including mouthwashes or rinses, mouth sprays, dental solutions and irrigation fluids. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion) and an anticalculus agent (from about 0.1% to about 3%). Components of dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

The present flavor system is particularly advantageous in masking the unpleasant aesthetics due to peroxide in such liquid products. In such products, the peroxide is pre-solubilized and readily available to stimulate the nerves and taste receptors in the mouth when the product is introduced therein. During use of a semi-solid product such as a toothpaste, relatively lower levels of peroxide are available to produce a sensory effect since the peroxide is slowly solubilized with saliva during toothbrushing.

Types of orally acceptable carriers or excipients which may be included in compositions of the present invention, along with specific non-limiting examples, are discussed in the following paragraphs.

Tooth Substantive Agent

The present invention may include a tooth substantive agent such as polymeric surface active agents (PMSA's), which are polyelectrolytes, more specifically anionic polymers. The PMSA's contain anionic groups, e.g., phosphate, phosphonate, carboxy, or mixtures thereof, and thus, have the capability to interact with cationic or positively charged entities. The "mineral" descriptor is intended to convey that the surface activity or substantivity of the polymer is toward mineral surfaces such as calcium phosphate minerals or teeth.

PMSA's are useful in the present compositions because of their stain prevention benefit. It is believed the PMSA's provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSA's on teeth can also prevent stains from accruing due to disruption of binding sites of color bodies on tooth surfaces.

The ability of PMSA's to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers.

The desired surface effects include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

The polymeric mineral surface active agents include any agent which will have a strong affinity for the tooth surface, deposit a polymer layer or coating on the tooth surface and produce the desired surface modification effects. Suitable examples of such polymers are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789, 5,093,170; 5,009,882; and 4,939,284; all to Degenhardt et al. and the diphosphonate-derivatized polymers in U.S. Pat. No. 5,011,913 to Benedict et al; the synthetic anionic polymers including polyacrylates and copolymers of maleic anhydride or acid and methyl vinyl ether (e.g., Gantrez), as described, for example, in U.S. Pat. No. 4,627,977, to Gaffar et al. A preferred polymer is diphosphonate modified polyacrylic acid. Polymers with activity must have sufficient surface binding propensity to desorb pellicle proteins and remain affixed to enamel surfaces. For tooth surfaces, polymers with end or side chain phosphate or phosphonate functions are preferred although other polymers with mineral binding activity may prove effective depending upon adsorption affinity.

Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Additional polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other suitable polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers), such as those having the following structure:

1. Co-Telomer of Acrylic Acid and
2-(hydroxyphosphinyl)ethylidene-1,1-diphosphonic acid with Structure

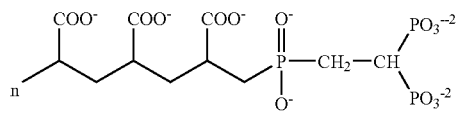

2. Co-Polymer of Acrylic Acid and
Vinyldiphosphonic Acid with Structure

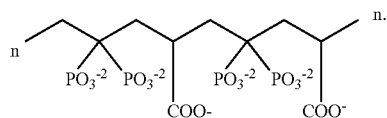

Suitable polymers include the diphosphonate/acrylate polymers supplied by Rhodia under the designation ITC 1087 (Average MW 3000-60,000) and Polymer 1154 (Average MW 6000-55,000).

A preferred PMSA will be stable with other components of the oral care composition such as ionic fluoride and metal ions. Also preferred are polymers that have limited hydrolysis in high water content formulations, thus permitting a simple single phase dentifrice or mouthrinse formulation. If the PMSA does not have these stability properties, one option is a dual phase formulation with the polymeric mineral surface active agent separated from the fluoride or other incompatible component. Another option is to formulate non-aqueous, essentially non-aqueous or limited water compositions to minimize reaction between the PMSA and other components.

A preferred PMSA is a polyphosphate. A polyphosphate is generally understood to consist of two or more phosphate molecules arranged primarily in a linear configuration, although some cyclic derivatives may be present. Although pyrophosphates (n=2) are technically polyphosphates, the polyphosphates desired are those having around three or more phosphate groups so that surface adsorption at effective concentrations produces sufficient non-bound phosphate functions, which enhance the anionic surface charge as well as hydrophilic character of the surfaces. The inorganic polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear polyphosphates having the formula:

wherein X is sodium, potassium or ammonium and n averages from about 3 to about 125. Preferred polyphosphates are those having n averaging from about 6 to about 21, such as those commercially known as Sodaphos (n≈6), Hexaphos (n≈13), and Glass H (n≈21) and manufactured by FMC Corporation and Astaris. These polyphosphates may be used alone or in combination. Polyphosphates are susceptible to hydrolysis in high water formulations at acid pH, particularly below pH 5. Thus it is preferred to use longer-chain polyphosphates, in particular Glass H with an average chain length of about 21. It is believed such longer-chain polyphosphates when undergoing hydrolysis produce shorter-chain polyphosphates which are still effective to deposit onto teeth and provide a stain preventive benefit.

Other polyphosphorylated compounds may be used in addition to or instead of the polyphosphate, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

The amount of tooth substantive agent will typically be from about 0.1% to about 35% by weight of the total oral composition. In dentifrice formulations, the amount is preferably from about 2% to about 30%, more preferably from about 5% to about 25%, and most preferably from about 6% to about 20%. In mouthrinse compositions, the amount of tooth substantive agent is preferably from about 0.1% to 5% and more preferably from about 0.5% to about 3%.

In addition to creating the surface modifying effects, the tooth substantive agent may also function to solubilize insoluble salts. For example, Glass H has been found to solubilize insoluble stannous salts. Thus, in compositions containing stannous fluoride for example, Glass H contributes to decreasing the stain promoting effect of stannous.

Fluoride Source

It is common to have a water-soluble fluoride compound present in dentifrices and other oral compositions in an amount sufficient to give a fluoride ion concentration in the composition, and/or when it is used of from about 0.0025% to about 5.0% by weight, preferably from about 0.005% to about 2.0% by weight, to provide anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include: stannous fluoride, sodium fluoride, potassium fluoride, sodium monofluorophosphate, indium fluoride and many others. Stannous fluoride and sodium fluoride are preferred, as well as mixtures thereof.

Abrasives

Dental abrasives useful in the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in Wason, U.S. Pat. No. 4,340,583, issued Jul. 29, 1982; and in commonly-assigned U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued Jul. 29, 1997, and U.S. Pat. No. 6,740,311, issued May 25, 2004.

Mixtures of abrasives can be used such as mixtures of the various grades of Zeodent® silica abrasives listed above. The total amount of abrasive in dentifrice compositions of the subject invention typically range from about 6% to about 70% by weight; toothpastes preferably contain from about 10% to about 50% of abrasives, by weight of the composition. Dental solution, mouth spray, mouthwash and non-abrasive gel compositions of the subject invention typically contain little or no abrasive.

Anticalculus Agent

The present compositions may optionally include an additional anticalculus agent, such as a pyrophosphate salt as a source of pyrophosphate ion. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, from about 1.5% to about 10% in one embodiment, and from about 2% to about 6% in another embodiment. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is a preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in *Kirk-Othmer Encyclopedia of Chemical Technology*, Third Edition, Volume 17, Wiley-Interscience Publishers (1982).

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., as well as, e.g., polyamino propane sulfonic acid (AMPS), diphosphonates (e.g., EHDP; AHP), polypeptides (such as polyaspartic and polyglutamic acids), and mixtures thereof.

Chelating Agents

Another optional agent is a chelating agent, also called sequestrants, such as gluconic acid, tartaric acid, citric acid and pharmaceutically-acceptable salts thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention. Suitable chelating agents will generally have a calcium binding constant of about $10^1$ to $10^5$ to provide improved cleaning with reduced plaque and calculus formation. Chelating agents also have the ability to complex with metallic ions and thus aid in preventing their adverse effects on the stability or appearance of products. Chelation of ions, such as iron or copper, helps retard oxidative deterioration of finished products.

Examples of suitable chelating agents are sodium or potassium gluconate and citrate; citric acid/alkali metal citrate combination; disodium tartrate; dipotassium tartrate; sodium potassium tartrate; sodium hydrogen tartrate; potassium hydrogen tartrate; sodium, potassium or ammonium polyphosphates and mixtures thereof. The amounts of chelating agent suitable for use in the present invention are about 0.1% to about 2.5%, preferably from about 0.5% to about 2.5% and more preferably from about 1.0% to about 2.5%.

Still other chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2.

Other Active Agents

The present invention may optionally include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, and triclosan monophosphate. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl(2-phenoxyethyl)ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206,215, issued Jun. 3, 1980, to Bailey. Other antimicrobials such as copper salts, zinc salts and stannous salts may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Preferred antimicrobial agents include zinc salts, stannous salts, cetyl pyridinium chloride, chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents provide anti-plaque benefits and are typically present at levels of from about 0.01% to about 5.0%, by weight of the composition.

Another optional active agent that may be added to the present compositions is a dentinal desensitizing agent to control hypersensitivity, such as salts of potassium, calcium, strontium and tin including nitrate, chloride, fluoride, phosphates, pyrophosphate, polyphosphate, citrate, oxalate and sulfate.

Surfactants

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. The present composition typically comprises an anionic surfactant at a level of from about 0.025% to about 9%, from about 0.05% to about 5% in some embodiments, and from about 0.1% to about 1% in other embodiments.

Another suitable surfactant is one selected from the group consisting of sarcosinate surfactants, isethionate surfactants and taurate surfactants. Preferred for use herein are alkali metal or ammonium salts of these surfactants such as the sodium and potassium salts of the following: lauroyl sarcosinate, myristoyl sarcosinate, palmitoyl sarcosinate, stearoyl sarcosinate and oleoyl sarcosinate. The sarcosinate surfactant may be present in the compositions of the present invention from about 0.1% to about 2.5%, preferably from about 0.5% to about 2.0% by weight of the total composition.

Cationic surfactants useful in the present invention include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., where said quaternary ammonium fluorides have detergent properties. Certain cationic surfactants can also act as germicides in the compositions disclosed herein. Cationic surfactants such as chlorhexidine, although suitable for use in the current invention, are not preferred due to their capacity to stain the oral cavity's hard tissues. Persons skilled in the art are aware of this possibility and should incorporate cationic surfactants with this limitation in mind.

Nonionic surfactants that can be used in the compositions of the present invention include compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Suitable betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice include cocoamidopropyl betaines and preferably, the lauramidopropyl betaine.

Thickening Agents

In preparing toothpaste or gels, thickening agents are added to provide a desirable consistency to the composition, to provide desirable active release characteristics upon use, to provide shelf stability, and to provide stability of the composition, etc. Suitable thickening agents include one or a combination of carboxyvinyl polymers, carrageenan, hydroxyethyl cellulose (HEC), natural and synthetic clays (e.g., Veegum and laponite) and water soluble salts of cellulose ethers such as sodium carboxymethylcellulose (CMC) and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Suitable carboxyvinyl polymers useful as thickening or gelling agents include carbomers which are homopolymers of acrylic acid crosslinked with an alkyl ether of pentaerythritol or an alkyl ether of sucrose. Carbomers are commercially available from B.F. Goodrich as the Carbopol® series, including Carbopol 934, 940, 941, 956, and mixtures thereof.

Thickening agents are typically present in an amount from about 0.1% to about 15%, preferably from about 2% to about 10%, more preferably from about 4% to about 8%, by weight of the total toothpaste or gel composition, can be used. Higher concentrations may be used for chewing gums, lozenges and breath mints, sachets, non-abrasive gels and subgingival gels.

Humectants

Another optional carrier material of the present compositions is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, propylene glycol and trimethyl glycine.

Miscellaneous Carrier Materials

Water employed in the preparation of commercially suitable oral compositions should preferably be of low ion content and free of organic impurities. Water may comprise up to about 99% by weight of the aqueous compositions herein. These amounts of water include the free water which is added plus that which is introduced with other materials, such as with sorbitol.

The present invention may also include an alkali metal bicarbonate salt, which may serve a number of functions including abrasive, deodorant, buffering and adjusting pH. Alkali metal bicarbonate salts are soluble in water and unless stabilized, tend to release carbon dioxide in an aqueous system. Sodium bicarbonate, also known as baking soda, is a commonly used alkali metal bicarbonate salt. The present composition may contain from about 0.5% to about 30%, preferably from about 0.5% to about 15%, and most preferably from about 0.5% to about 5% of an alkali metal bicarbonate salt.

The pH of the present compositions may be adjusted through the use of buffering agents. Buffering agents, as used herein, refer to agents that can be used to adjust the pH of aqueous compositions such as mouthrinses and dental solutions preferably to a range of about pH 4.0 to about pH 6.0 for peroxide stability. Buffering agents include sodium bicarbonate, monosodium phosphate, trisodium phosphate, sodium hydroxide, sodium carbonate, sodium acid pyrophosphate, citric acid, and sodium citrate. Buffering agents are typically included at a level of from about 0.5% to about 10%, by weight of the present compositions.

Poloxamers may be employed in the present compositions. A poloxamer is classified as a nonionic surfactant and may also function as an emulsifying agent, binder, stabilizer, and other related functions. Poloxamers are difunctional block-polymers terminating in primary hydroxyl groups with molecular weights ranging from 1,000 to above 15,000. Poloxamers are sold under the tradename of Pluronics and Pluraflo by BASF. Suitable poloxamers for this invention are Poloxamer 407 and Pluraflo MA370.

Other emulsifying agents that may be used in the present compositions include polymeric emulsifiers such as the Pemulen® series available from B.F. Goodrich, and which are predominantly high molecular weight polyacrylic acid polymers useful as emulsifiers for hydrophobic substances.

Titanium dioxide may also be added to the present composition. Titanium dioxide is a white powder which adds opacity to the compositions. Titanium dioxide generally comprises from about 0.25% to about 5% by weight of dentifrice compositions.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the trade name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits.

Method of Use

The present invention also relates to methods for whitening teeth and preventing staining. The benefits of these compositions may increase over time when the composition is used repeatedly.

The method of treatment herein comprises contacting a subject's dental enamel surfaces and mucosa in the mouth with the oral compositions according to the present invention. The method of treatment may be by brushing with a dentifrice or rinsing with a dentifrice slurry or mouthrinse. Other methods include contacting the topical oral gel, dentures product, mouthspray, or other form with the subject's teeth and oral mucosa. The subject may be any person or animal whose tooth surface contact the oral composition. By animal is meant to include household pets or other domestic animals, or animals kept in captivity.

For example, a method of treatment may include a person brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Example I

Mouthrinse Compositions

Mouthrinse compositions according to the present invention (IA-IF) are shown below with amounts of components in weight %. These compositions are made using conventional methods. The mouthrinse compositions were judged in consumer testing as having a pleasant high-impact minty taste during use and providing noticeable fresh breath.

| Ingredient | Ex. IA | Ex. IB | Ex. IC | Ex. ID | Ex. IE | Ex. IF |
|---|---|---|---|---|---|---|
| 35% $H_2O_2$ solution | 4.286 | 4.286 | 4.286 | 2.143 | 4.286 | 4.286 |
| Menthol | 0.075 | 0.020 | 0.040 | 0.040 | 0.030 | 0.040 |
| WS-3 Coolant | 0.020 | 0.030 | 0.020 | 0.020 | 0.015 | 0.025 |
| WS-23 Coolant |  | 0.020 | 0.010 |  | 0.015 | 0.010 |
| Artificial Mint Flavor[1] | 0.145 | 0.135 | 0.135 | 0.150 | 0.135 | 0.135 |
| Poloxamer 407 | 0.750 | 0.750 | 0.750 | 0.100 | 0.100 | 0.100 |
| Glycerin | 11.000 | 11.000 | 11.000 | 20.000 | 20.000 | 20.000 |
| Propylene Glycol | 3.000 | 3.000 |  | 4.000 | 4.000 | 4.000 |
| Sucralose |  | 0.050 | — | — |  |  |
| Sodium Saccharin | 0.080 | — | 0.068 | 0.060 | 0.080 | 0.060 |
| Polyphosphate[2] |  | 2.0 | 1.000 |  |  |  |
| Cetyl Pyridinium Chloride |  |  |  | 0.074 | 0.100 | 0.100 |
| Na Citrate | 0.212 | 0.212 |  |  |  |  |
| Citric Acid | 0.052 | 0.052 | 0.052 |  |  |  |
| Alcohol, USP |  |  | 5.000 |  |  |  |
| Water, Purified, USP | QS | QS | QS | QS | QS | QS |

[1]Artificial Mint Flavor comprises methyl salicylate, cinnnamic alcohol, eucalyptol, menthone and other flavor agents. A mint flavor comprising natural oils (peppermint, anise, clove bud oil, sweet birch) may be used instead of the artificial mint flavor.
[2]Polyphosphate is Glass H (n ≈ 21) supplied by Astaris.

Example II

Dual-Phase Dentifrice Compositions

Dual phase dentifrice compositions according to the present invention are comprised of a first dentifrice composition (IIA-IIC) containing peroxide and a second dentifrice composition (IID-IIE), dispensed preferably at a 50:50 ratio. These compositions are made using conventional methods.

| Ingredient | First Dentifrice | | | Second Dentifrice | | |
|---|---|---|---|---|---|---|
|  | IIA | IIB | IIC | IID | IIE | IIF |
| Glass H Polyphosphate | 7.00 | 7.00 |  |  |  |  |
| Sodaphos Polyphosphate |  |  | 7.00 |  |  |  |
| Calcium Peroxide | 1.00 | 0.40 | 5.00 |  |  |  |
| Sodium Fluoride |  |  |  | 0.486 | 0.486 |  |
| Stannous Fluoride |  |  |  |  |  | 0.908 |
| Stannous Chloride |  |  |  |  |  | 3.000 |
| Sodium Gluconate |  |  |  |  |  | 4.160 |
| Carboxymethycellulose | 0.60 | 0.60 | 0.60 |  |  |  |

-continued

| Ingredient | First Dentifrice | | | Second Dentifrice | | |
|---|---|---|---|---|---|---|
| | IIA | IIB | IIC | IID | IIE | IIF |
| Carbomer | | | | | 0.20 | |
| Artificial Mint Flavor[1] | 1.00 | 1.00 | 1.00 | 0.40 | 0.90 | 1.00 |
| Menthol | 0.075 | 0.020 | 0.040 | | | |
| WS-3 Coolant | 0.020 | 0.030 | 0.020 | | | |
| WS-23 Coolant | | 0.020 | 0.010 | 0.30 | 0.40 | 0.40 |
| Color | | | | 0.30 | 0.40 | 0.30 |
| Glycerin | 43.20 | 26.80 | 24.20 | 44.514 | 9.00 | 28.992 |
| Sorbitol | | | | | 29.594 | |
| Poloxamer 407 | 5.00 | 5.00 | 5.00 | 21.00 | | 15.500 |
| Polyethylene Glycol | 3.00 | 3.00 | 3.00 | | 3.00 | |
| Propylene Glycol | 5.00 | 5.00 | 5.00 | | | |
| Sodium Alkyl Sulfate[2] | 4.00 | 4.00 | 4.00 | | 4.00 | |
| Silica | 20.00 | 22.00 | 22.00 | | 22.50 | 23.000 |
| Sodium Hydroxide[3] | | | | | | 1.000 |
| Sodium Bicarbonate | | 15.00 | 15.00 | | | |
| Sodium Carbonate | 2.00 | 2.00 | 2.00 | | | |
| Sodium Saccharin | 0.50 | 0.50 | 0.50 | 0.30 | 0.50 | 0.30 |
| Titanium Dioxide | 0.50 | 0.50 | 0.50 | | | |
| Xanthan Gum | 0.20 | 0.20 | 0.20 | | 0.60 | |
| Sodium Acid Pyrophosphate | | | | | 0.50 | |
| Tetrasodium Pyrophosphate | | | | | 3.22 | |
| Water | QS | QS | QS | QS | QS | QS |

[1]Artificial Mint Flavor comprises methyl salicylate, cinnnamic alcohol, eucalyptol, menthone and other flavor agents. A mint flavor comprising natural oils (peppermint, anise, clove bud oil, sweet birch) may be used instead of the artificial mint flavor.
[2]27.9% solution
[3]50% solution The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition in liquid form selected from mouthrinse, mouth spray, dental solution and irrigation fluid comprising
   (a) from about 0.01% to about 30% by weight of the composition of a pre-solubilized peroxide source,
   (b) a flavor composition comprising a coolant combination of menthol and at least one secondary coolant and a mixture of flavor components that maintain a consistent flavor profile in the presence of peroxide comprising methyl salicylate, cinnamic alcohol, eucalyptol, and menthone, wherein the menthol and secondary coolant combination comprises from about 0.03% to about 1.5% and menthol comprises at least about 0.015% or more by weight of the oral care composition, and
   (c) an orally-acceptable carrier,
   wherein the composition has a pH of about 4.0 to about 6.0 for peroxide stability and wherein the flavor composition effectively masks undesirable aesthetics derived from peroxide and provides a high impact refreshing taste and sensation.

2. An oral care composition according to claim 1 wherein the peroxide source is selected from the group consisting of peroxides, perborates, percarbonates, peroxyacids, persulfates, and mixtures thereof.

3. An oral care composition according to claim 1 wherein the peroxide source is selected from the group consisting of hydrogen peroxide, urea peroxide, sodium percarbonate, and mixtures thereof.

4. An oral care composition according to claim 1 wherein the secondary coolant is selected from carboxamides, ketals, diols, menthyl esters and mixtures thereof.

5. An aqueous oral care composition according to claim 1, further comprising an antimicrobial active selected from cetyl pyridinium chloride, domiphen bromide, zinc salts, stannous salts, chlorhexidine, triclosan, triclosan monophosphate and mixtures thereof.

6. An oral care composition according to claim 1 in the form of a mouthrinse.

7. An oral care composition in liquid form selected from mouthrinse, mouth spray, dental solution and irrigation fluid comprising
   (a) from about 0.01% to about 10% by weight of the composition of a pre-solubilized peroxide source selected from hydrogen peroxide or urea peroxide,
   (b) from about 0.03% to about 0.6% by weight of the composition of a coolant combination of menthol and at least one secondary coolant, wherein menthol comprises about 0.015% or more by weight of the composition, (c) a mixture of flavor components comprising methyl salicylate, cinnamic alcohol, eucalyptol, and menthone, and (d) an orally-acceptable aqueous carrier, wherein the composition has a pH of about 4.0 to about 6.0 for peroxide stability and wherein undesirable aesthetics derived from peroxide are effectively masked and the composition provides a consistent flavor profile and a high impact refreshing taste and sensation.

8. An aqueous oral care composition according to claim 7 wherein the secondary coolant is selected from carboxamides, ketals, diols, menthyl esters and mixtures thereof.

9. An aqueous oral care composition according to claim 7, further comprising an antimicrobial active selected from cetyl pyridinium chloride, domiphen bromide, zinc salts, stannous salts, chlorhexidine, triclosan, triclosan monophosphate and mixtures thereof.

* * * * *